(12) United States Patent
Lippert et al.

(10) Patent No.: US 9,314,411 B2
(45) Date of Patent: *Apr. 19, 2016

(54) SILICA ABRASIVE-FREE DENTIFRICE COMPOSITION

(71) Applicant: Glaxo Group Limited, Brentford, Middlesex (GB)

(72) Inventors: Frank Lippert, Surrey (GB); Robert Anthony Lucas, Surrey (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/659,720

(22) Filed: Mar. 17, 2015

(65) Prior Publication Data

US 2015/0182427 A1 Jul. 2, 2015

Related U.S. Application Data

(63) Continuation of application No. 13/637,100, filed as application No. PCT/EP2011/054770 on Mar. 29, 2011, now Pat. No. 9,011,824.

(30) Foreign Application Priority Data

Mar. 31, 2010 (GB) .................................. 1005508.5

(51) Int. Cl.
| | | |
|---|---|---|
| A61Q 11/00 | (2006.01) | |
| A61Q 11/02 | (2006.01) | |
| A61K 8/26 | (2006.01) | |
| A61K 8/24 | (2006.01) | |
| A61K 6/00 | (2006.01) | |
| A61K 8/21 | (2006.01) | |

(52) U.S. Cl.
CPC ... *A61K 8/26* (2013.01); *A61K 8/21* (2013.01); *A61K 8/24* (2013.01); *A61Q 11/00* (2013.01); *A61K 2800/30* (2013.01); *A61K 2800/34* (2013.01); *A61K 2800/412* (2013.01); *A61K 2800/592* (2013.01)

(58) Field of Classification Search
CPC . A61Q 11/00; A61Q 11/02; A61K 2800/412; A61K 8/26; A61K 8/24
USPC ...................................................... 424/49, 57
See application file for complete search history.

(56) References Cited

U.S. PATENT DOCUMENTS

| | | |
|---|---|---|
| 4,632,826 A | 12/1986 | Ploger et al. |
| 5,184,304 A | 2/1993 | Huddle |
| 5,698,182 A | 12/1997 | Prencipe et al. |
| 6,174,516 B1 | 1/2001 | Curtis et al. |
| 6,517,815 B1 | 2/2003 | Leinen et al. |
| 6,682,717 B1 | 1/2004 | Wills et al. |
| 2006/0222602 A1 | 10/2006 | Barth et al. |

FOREIGN PATENT DOCUMENTS

| | | |
|---|---|---|
| CA | 1259927 | 9/1989 |
| JP | 58 057311 A | 4/1983 |
| WO | WO 95/17158 | 6/1995 |
| WO | WO 00/48563 A1 | 8/2000 |

OTHER PUBLICATIONS

Colgate. Dental Caries (Cavities), Jan. 10, 2011.

*Primary Examiner* — Robert A Wax
*Assistant Examiner* — Tracy Liu
(74) *Attorney, Agent, or Firm* — Nora L. Stein; Theodore R. Furman

(57) ABSTRACT

A dentifrice composition providing superior shine and polish, low RDA and effective whitening comprising a calcined aluminum oxide polishing agent, a water soluble condensed phosphate such as an alkali metal phosphate salt and an orally acceptable carrier or excipient is described. The composition is free of a silica abrasive.

8 Claims, 5 Drawing Sheets

FIGURE 1

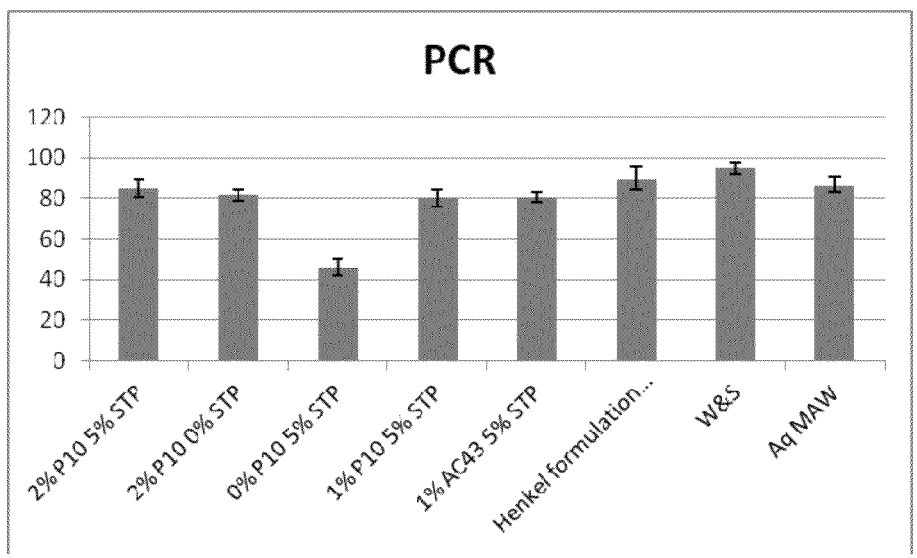

Figure 1: PCR results demonstrate that the inclusion of STP together with a low calcined alumina enhances the cleaning performance of a dentifrice solely comprising a low calcined alumina. Whilst the Henkel formulation, further comprising silica, also has good cleaning performance this is at the expense of significantly increasing the abrasivity of the formulation as determined in the RDA methodology, the result being described in Figure 2.

Figure 2: This graph depicts the relative dentin abrasiveness (RDA) of each of the test materials, including commercial toothpaste formulations and formulations of the invention.

Figure 3: This graph depicts the Cleaning Efficiency Index (CEI) which is the PCR/RDA values from Figure 1 and Figure 2.

Figure 4: This graph depicts gloss measurements taken before and after brushing with a Novo-Curve small area glossmeter.

Figure 5: This graph depicts the Gloss Efficiency Index which is the Gloss/RDA value.

SILICA ABRASIVE-FREE DENTIFRICE COMPOSITION

FIELD OF THE INVENTION

This invention relates to dentifrice compositions comprising an aluminium oxide (alumina) polishing agent and a condensed phosphate (such as a water soluble alkali metal polyphosphate salt) which, in the absence of any silica abrasive material, can effectively whiten and polish the enamel of teeth and the surface of dental prostheses without a high degree of abrasion and scratching of the enamel surface. Such dentifrice compositions thereby provide good cleaning of tooth surfaces, the effectiveness of which is improved by the absence of a silica abrasive material.

BACKGROUND OF THE INVENTION

Dentifrices are used to clean the teeth, generally with toothpaste and a toothbrush and on a daily basis. The toothpaste will aid in the removal of food particles and tooth discolouration caused by substances such as tobacco, tea or wine in addition to the removal of plaque from the surface of the teeth. Toothpastes will also polish the teeth. Cleaning and polishing the tooth surfaces are affected by (1) mechanical means such as abrasive substances and (2) chemical processes such as materials that dissolve the discolouration.

Over-the-counter teeth whitening preparations have been developed to address the cosmetic preference of many to restore luster to tooth enamel discolored by surface entrapped materials; the term lightening may also be used in conjunction with the advertising and sale of these products. While all dentifrices and mouthwashes contain some cleaning and polishing agents some enamel deposits are not removed completely by these agents under normal use conditions. These preparations may not be formulated with the amount or type of agent required to remove the amount of stains and discoloration which build up due to excessive exposure to the staining agent. For example, smokers often develop discolored enamel because the tars and particulate in exhaled cigarette smoke collect on the teeth. And a number of comestibles can stain or discolor tooth enamel, tea being one example of a beverage where the tannins in the tea quickly deposit on the tooth enamel. Some medicinal agents may cause staining or discoloration via entrapment, though this is not a usual common cause of this type of staining.

Accordingly it has become highly desirable to include within an oral healthcare product materials that will both whiten and gloss the enamel of the tooth surface.

Traditionally, effective whitening and good gloss has been associated with high dentine abrasivity (RDA) values. The RDA of a particular substance or formulation can be readily determined by one skilled in the art. See "A Laboratory Method for Assessment of Dentifrice Abrasivity" John J. Hefferen, Journal of Dental Research, Vol 55, No. 4, 536-573.

The technology of the present invention allows compositions to deliver superior gloss, maximise cleaning and provide effective whitening with a significantly lower RDA value than traditional whitening toothpastes.

Oral healthcare compositions containing water soluble polyphosphate (also known as condensed phosphate) salts such as tripolyphosphate salts, are known for use as chemical agents to clean and whiten the teeth.

WO95/17158 (SmithKline Beecham Corp) discloses and claims a composition for reducing or removing surface deposited stains from natural teeth and dental prostheses comprising a dentally acceptable preparation comprising about 5 to 15% by weight of a water soluble alkali metal tripolyphosphate. Suitably the water soluble alkali metal tripolyphosphate is sodium tripolyphosphate.

WO2005/027858 (Glaxo Group Ltd) relates to dentifrice compositions, in particular compositions comprising a fluoride source and a soluble calcium sequestering agent that is not an oxidising agent, for cleaning natural teeth and dentures. Such compositions show excellent cleaning properties whilst at the same time low abrasion characteristics. These compositions must have an RDA value of below 30 and an IVSR value greater than 50 (when compared to a Control). The calcium sequestering agent, which is present in a proportion of 1-20 wt %, may be a condensed phosphate salt, such as sodium tripolyphosphate. An abrasive material may also be present in a proportion of 0-5 wt % of the composition.

U.S. Pat. No. 6,517,815 (Henkel Kommanditgesellschaft auf Aktien) discloses a dentifrice in the form of an aqueous paste or liquid dispersion, comprising 10% to 30% by weight of a combination of silica polishing agents and aluminium oxide in a ratio by weight of 10:0.2 to 10:2, 20% to 50% by weight of a humectants and 2% to 12% by weight of a condensed phosphate. The condensed phosphates are in the form of an alkali metal or ammonium salt. The aluminium oxide is preferably a lightly calcined alumina with a content of at least 10% by weight of α-aluminium oxide of various γ-aluminium oxides. It is suggested that the special combination of polishing agents (ie the combination of the silica and the alumina) is able to provide a dentifrice having good polishing and cleaning effects with only moderate dentine and enamel abrasion, notwithstanding the presence of the hard alumina polishing component.

U.S. Pat. No. 4,632,826 (Henkel Kommanditgesellschaft auf Aktien) discloses a tooth cream comprising 100 parts by weight of silica polishing agent and 2 to 15 parts by weight of weakly calcined alumina polishing agent. The silica polishing agent consists essentially of silica hydrogel and precipitated silica and the weakly calcined alumina 10 to 50% by weight of gamma aluminium oxide and 50 to 90% by weight of alpha aluminium oxide. The tooth cream is suitable for removing stain, polishing and cleaning the surface of teeth without producing any deep scratches or damage by daily use.

Klüppel et al. *J. Soc. Cosmet. Chem.,* 37, 211-223 (July/August 1986) "Parameters for assessing the cleaning power of toothpastes" compares a number of dentifrice formulations for polishing and scratching effects. Test formulations are described containing as the sole abrasive material either a polishing alumina or a hydrated silica or a mixture of a hydrated silica with a polishing alumina. The results suggest that dentifrice products can be developed with high cleaning power and low dentine abrasion. Whilst the test formulations with increasing amounts of a polishing alumina, as the sole abrasive, can provide good cleaning power this was coupled with an unacceptable increase in enamel abrasion. The best test formulation contained a mixture of a silica abrasive and an alumina abrasive which exhibited a high cleaning value together with an unexpectedly low enamel abrasion value.

It has now been found that dentifrice compositions comprising an aluminium oxide polishing agent and a water soluble condensed phosphate salt (such as an alkali metal tripolyphosphate) in the absence of a silica abrasive material exhibit highly effective cleaning power, excellent gloss and shine whilst at the same time providing low dentine abrasion to the tooth surface. In addition, these dentifrice compositions show superior properties when compared to a corresponding formulation that contains an aluminium oxide polishing agent, a water soluble condensed phosphate salt and a silica abrasive.

DETAILED DESCRIPTION OF THE INVENTION

Brief Description of the Drawings

FIG. 1 is a graphic depiction of the Pellicle Cleaning Ratio (PCR) of formulations according to the invention containing STP together with a low-calcined alumina compared to commercial formulations and formulations without the inventive combination.

Figure 2:
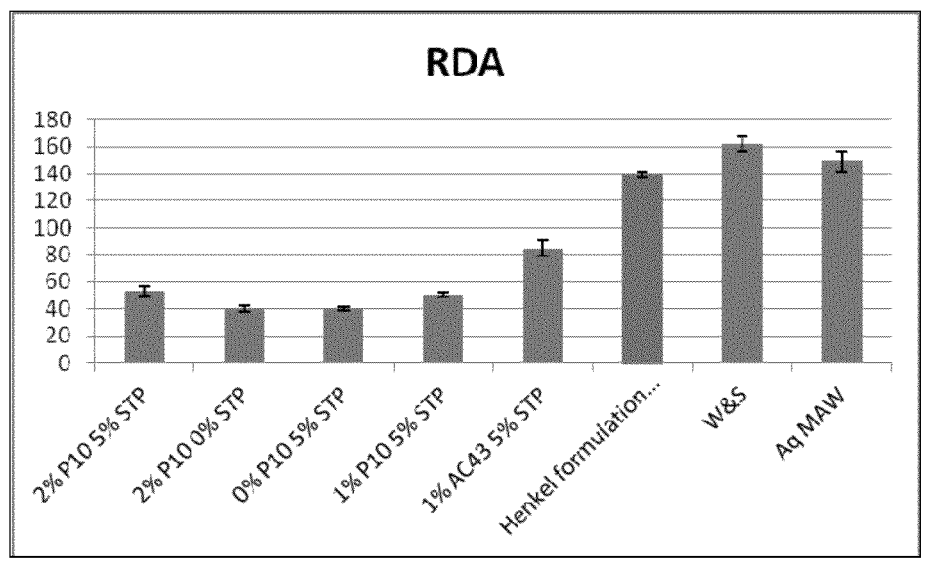
FIG. 2 is a graphic depiction of the RDA of each of the test materials.

Accordingly the present invention provides a dentifrice composition comprising a calcined aluminium oxide polishing agent, a water soluble condensed phosphate and an orally acceptable carrier or excipient; the composition being free of a silica abrasive.

Compositions of the present invention show particularly good polishing, gloss and cleaning of the tooth surface, whilst minimising dentine abrasivity, as shown in the data below. Such compositions also have acceptable enamel abrasivity.

Compositions of the present invention can therefore provide, after brushing, highly polished and smoother tooth surfaces, which may attract less plaque, tartar and/or stain resulting in an overall improvement in oral health.

Aluminium oxide polishes having various degrees of calcination, fineness and powder densities are commercially available. In the present invention a preferred aluminium oxide polish is a low calcined alumina, for example as described in the above noted Henkel patents, suitably comprising from 50% to 90% by weight of α-aluminium oxide and 10% to 50% of γ-aluminium oxide.

Suitable low calcined aluminas are prepared by mild or weak calcination from aluminium hydroxide. Aluminium hydroxide is converted by calcination into α-aluminium oxide ($Al_2O_3$), which is thermodynamically stable at temperatures above 1200° C. The thermodynamically unstable $Al_2O_3$ forms occurring at temperatures between 400 to 1000° C. are known as γ-forms. The degree of calcination, i.e. the conversion into thermodynamically stable α-aluminium oxide ($Al_2O_3$) can be adjusted as required through the choice of temperature and duration of the calcination process. Low calcination gives an alumina with a low α-$Al_2O_3$ content and higher γ-$Al_2O_3$ compared to high calcination. As the calcinations temperature and time increases, the amount of α-$Al_2O_3$ increases and the amount of γ-$Al_2O_3$ decreases. These are distinguished from pure α-$Al_2O_3$ by a lower hardness of the agglomerate, a larger specific surface and larger pore volumes.

A low calcined aluminia suitable for the present invention is P10 Feinst available from Almatis which is a high polishing alumina having a primary crystal size of <1 micron and an α-$Al_2O_3$ content >70%. P10 Feinst is available from Almatis GmbH, Giulinistrasse 2, 67065 Ludwigshafen, Germany. (see also http://www.almatis.com/download/data-sheets/GP-RCP_007_Calcined_Aluminas_for_Polishing_1009.pdf Suitably the low calcined alumina is present in an amount from 0.1% to 3.0%, for example from 0.2% to 3.0% or 0.5% to 2.0% by weight of the total composition.

A further component of the compositions of this invention is a water soluble condensed phosphate salt, such as an alkali metal pyrophosphate, tripolyphosphate or higher polyphosphate salt, in particular a water soluble alkali metal tripolyphosphate salt. Suitably the sodium form of this salt is preferred, although the potassium or mixed sodium and potassium salts could be used as a preferred embodiment as well. All physical forms can be used, e.g. a hydrate or the dehydrated form.

Most suitably the water soluble alkali metal tripolyphosphate salt is sodium tripolyphosphate.

Suitably the water soluble condensed phosphate salt (such as an alkali metal tripolyphosphate salt) is present in an amount from 1.0% to 20.0%, for example from 2.0% to 15.0% or 5.0% to 10.0% by weight of the total composition.

In addition to the above ingredients, compositions of the present invention may comprise one or more active agents conventionally used in dentifrice compositions, for example, a fluoride source, a desensitising agent, an anti-bacterial agent, an anti-plaque agent, eg. isopropylmethylphenol (IPMP), an anti-calculus agent, an oral malodour agent, an anti-inflammatory agent, an anti-oxidant, an anti-fungal agent, wound healing agent or a mixture of at least two thereof. Such agents may be included at levels to provide the desired therapeutic effect.

Examples of desensitising agents include a tubule blocking agent or a nerve desensitising agent and mixtures thereof, for example as described in WO02/15809 (Block). Examples of desensitising agents include a strontium salt such as strontium chloride, strontium acetate or strontium nitrate or a potassium salt such as potassium citrate, potassium chloride, potassium bicarbonate, potassium gluconate and especially potassium nitrate.

A desensitising agent such as a potassium salt is generally present between 2% to 8% by weight of the total composition, for example 5% by weight of potassium nitrate may be used.

Suitable sources of fluoride ions for use in the compositions of the present invention include an alkali metal fluoride such as sodium fluoride, an alkali metal monofluorophosphate such a sodium monofluorophosphate, stannous fluoride, or an amine fluoride in an amount to provide from 25 to 3500 pm of fluoride ions, preferably from 100 to 1500 ppm. A typical fluoride source is sodium fluoride, for example the composition may contain 0.1 to 0.5% by weight of sodium fluoride, eg 0.204% by weight (equating to 923 ppm of fluoride ions), 0.2542% by weight (equating to 1150 ppm of fluoride ions) or 0.315% by weight (equating to 1426 ppm of fluoride ions).

Such fluoride ions help promote the remineralisation of teeth and can increase the acid resistance of dental hard tissues for combating caries, dental erosion (ie. acid wear) and/or tooth wear.

Compositions of the present invention will contain additional formulating agents such as, surfactants, humectants, non-abrasive (thickening) silicas, flavouring agents, sweetening agents, opacifying or colouring agents, preservatives and water, selected from those conventionally used in the oral hygiene composition art for such purposes.

Suitable surfactants for use in the present invention include anionic surfactants such as a sodium $C_{10-18}$alkyl sulphate, eg sodium lauryl sulphate. Sodium lauryl sulphate is generally considered to be anionic and strongly charged and is useful if high levels of foaming are desired when brushing teeth.

In addition to anionic surfactants, zwitterionic, amphoteric, cationic and non- or low-ionic surfactants may be used to aid foaming characteristics. When anionic and amphoteric surfactants are used together an optimised foaming system is achieved that will provide both improved mouth feel and good cleaning. Examples of amphoteric surfactants include long chain alkyl (eg. $C_{10}$-$C_{18}$ alkyl) betaines, such as the product marketed under the tradename 'Empigen BB' by Albright & Wilson and long chain alkyl amidoalkyl betaines such as cocamidopropylbetaine.

A particularly preferred example of an anionic/amphoteric surfactant combination for use in the present invention is sodium lauryl sulphate/cocamidopropylbetaine.

Suitably, the surfactant is present in the range 0.1 to 15%, for example from 0.5 to 10% or from 1.0 to 5% by weight of the total composition Suitable humectants for use in compositions of the invention include glycerin, xylitol, sorbitol, propylene glycol or polyethylene glycol, or mixtures of at least two thereof; which humectant may be present in the range from 10 to 80%, for example from 20 to 70% or from 30 to 60% by weight of the total composition.

It will be understood that compositions of the present invention may also be used outside the oral cavity, for the cleaning of dentures and the like.

The dentifrices of the present invention are typically formulated in the form of a paste that is suitable for containing in and dispensing from a laminate tube or a pump as conventionally used in the art. Additional examples may include bag-in-can or bag-on-valve delivery systems that utilise a foaming agent such as pentane or iso-pentane.

A typical process for making the composition of this invention involves admixing the ingredients, suitably under a vacuum, until a homogeneous mixture is obtained, and adjusting the pH if necessary.

In order to aid stability, products containing a condensed phosphate should have a high pH value so one or more pH regulators may be added to maintain the pH of the composition at between 7.0-10.0, especially at pH 8.5-9.5. A suitable pH regulator is sodium hydroxide.

The pH is measured when the composition is slurried with water in a 1:3 weight ratio of the composition to water.

EXAMPLES

Data from the following formulations were obtained.

| Material | Dentifrice Composition | | | |
|---|---|---|---|---|
| | Ex 1 % w/w | Ex 2 % w/w | Ex 3 % w/w | Ex 4 % w/w |
| Sorbitol, Liquid (Non-Crystallising) | 22.00 | 22.00 | 22.00 | 22.00 |
| Glycerol (Ph. Eur) | 10.00 | 10.00 | 10.00 | 10.00 |
| Polyethylene Glycol 300 | 3.00 | 3.00 | 3.00 | 3.00 |
| Alumina (P10 Feinst) | 2.00 | 2.00 | — | 1.00 |
| Sodium Tripolyphosphate | 5.00 | — | 5.00 | 5.00 |
| Sodium Lauryl Sulphate | 1.50 | 1.50 | 1.50 | 1.50 |
| Xanthan Gum | 0.50 | 0.50 | 0.50 | 0.50 |
| Carrageenan | 0.50 | 0.50 | 0.50 | 0.50 |
| Saccharin Sodium | 0.30 | 0.30 | 0.30 | 0.30 |
| Sodium Fluoride | 0.32 | 0.32 | 0.32 | 0.32 |
| Cocamidopropyl Betaine | 0.65 | 0.65 | 0.65 | 0.65 |
| Titanium Dioxide | 1.00 | 1.00 | 1.00 | 1.00 |
| Flavour | 1.10 | 1.10 | 1.10 | 1.10 |
| Sodium hydroxide | — | 0.00 | 0.00 | 0.23 |
| Purified Water | ad 100 | ad 100 | ad 100 | ad 100 |

Examples 1 and 4 fall within the scope of the present invention comprising a low calcined alumina in combination with STP. Examples 2 and 3 are comparative examples comprising either a low calcined alumina or STP. In addition to the above experimental formulations which correspond to the first four examples shown in the graphs below, Macleans White 'n' Shine (W+S), Aquafresh Multi Action Whitening (MAW) and Pearl Drops (Church & Dwight Co.) were also tested. AC43 is a micronized silica and the "Henkel formulation" contained STP a low calcined, alumina (Feinst P10) and silica. The Henkel formulation was prepared as described in U.S. Pat. No. 6,517,815.

PCR Methodology

Specimen Preparation

Bovine, permanent, central incisors were cut to obtain labial enamel specimens approximately 10×10 mm. The enamel specimens were then embedded in an autopolymerizing methacrylate resin so that only the enamel surfaces were exposed. The enamel surfaces were then smoothed and polished on a lapidary wheel and lightly etched to expedite stain accumulation and adherence. They were placed on a rotating rod (in 37° C. incubator) alternately exposing them to air and to a solution consisting of trypticase soy broth, tea, coffee, mucin, FeCl3, and *Micrococcus luteus* BA13. The staining broth was changed and specimens rinsed daily for seven days. After seven days, a darkly stained pellicle film was apparent on the enamel surfaces. Specimens were then rinsed, allowed to air dry, and refrigerated until use. All products were tested using specimens prepared at the same time.

Scoring and Set-Up

The amount of in vitro stain was graded photometrically using only the L value of the L*a*b* scale using a spectrophotometer (Minolta CM2600d.) The area of the specimens scored was a ¼-inch diameter circle in the center of the 10×10 mm enamel. Specimens with scores between 30 and 42 (30 being more darkly stained) were used. On the basis of these scores, the specimens were divided into groups of 16 specimens each, with each group having the same average baseline score.

Test Procedure

The specimens were then mounted on a mechanical V-8 cross-brushing machine equipped with soft nylon-filament (Oral-B 40) toothbrushes. Brush force on the enamel surface was adjusted to 150 g. The dentifrices were used as slurries prepared by mixing 25 grams of dentifrice with 40 ml of deionized water. The ADA abrasion reference material ($Ca_2P_2O_7$) was prepared by mixing 10 g in 50 ml of a 0.5% CMC solution. The specimens were brushed for 800 strokes (4½ minutes). To minimize mechanical variables, one specimen per group was brushed on each of the eight brushing heads. Fresh slurries were made after being used to brush four specimens. Following brushing, specimens were rinsed, blotted dry, and scored again for stain as previously described.

Calculations

The difference between the pre- and post-brushing stain scores was determined and the mean and standard error calculated for the reference group. The cleaning ratio for the reference material group was assigned a value of 100. The mean decrement of the reference group was divided into 100 to obtain a constant value to multiple times each individual test decrement within the study. The individual cleaning ratio of each specimen was then calculated (decrement X constant). The mean and SEM for each group (N=16) was then calculated using the individual cleaning ratios. The larger the value of the cleaning ratio, the greater the amount of stained pellicle removed in this test.

These PCR results (see FIG. 1) demonstrate that the inclusion of STP together with a low calcined alumina enhances the cleaning performance of a dentifrice solely comprising a low calcined alumina Whilst the Henkel formulation, further comprising silica, also has good cleaning performance this is at the expense of significantly increasing the abrasivity of the formulation as determined in the RDA methodology described below.

RDA Methodology
Specimen Preparation

The procedure used in this study was the Hefferren abrasivity test recommended by the ADA and ISO 11609 for determination of dentifrice relative abrasiveness in dentin.

Eight (8) human dentin specimens were subjected to neutron bombardments resulting in the formation of radioactive phosphorus (32P) within the specimens under the controlled conditions outlined by the ADA. The specimens were then mounted in methyl methacrylate so they would fit in a V-8 cross-brushing machine. The specimens were preconditioned by brushing for 1500-strokes, (soft Oral B-40; 150 g brush tension) using a slurry consisting of 10 g ADA reference material in 50 ml of a 0.5% CMC glycerin solution.

Procedure

Following the precondition run, the test was performed (150 g and 1500 strokes) using in a "sandwich design." Before and after being brushed with the test product (25 g/40 ml water) each tooth set was brushed with the ADA reference material (10 g of $Ca_2P_2O_7$/50 ml 0.5% CMC). The procedure was repeated additional times so that each product was assayed on each tooth set. The treatment design was a modified Latin Square design so that no treatment followed another treatment consistently.

Calculations

One ml samples were taken, weighed (~1 g), and added to 5 ml of "Ultima Gold" scintillation cocktail. The samples were mixed well and immediately put on the scintillation counter for radiation count. Following counting, the net counts per minute (CPM) values were divided by the weight of the sample to calculate the net CPM/gram per slurry. The net CPM/g of the pre and post ADA reference material for each of the test slurries was then calculated and averaged to use in the calculation of RDA (relative dentin abrasion) for the test material. The ADA reference material was assigned a value of 100 and its ratio to the test material was calculated. See FIG. 2.

The values obtained in the above PCR and RDA experiments were then used to obtain the following Cleaning Efficiency Index (CEI) which is the PCR/RDA value.

Figure 3:
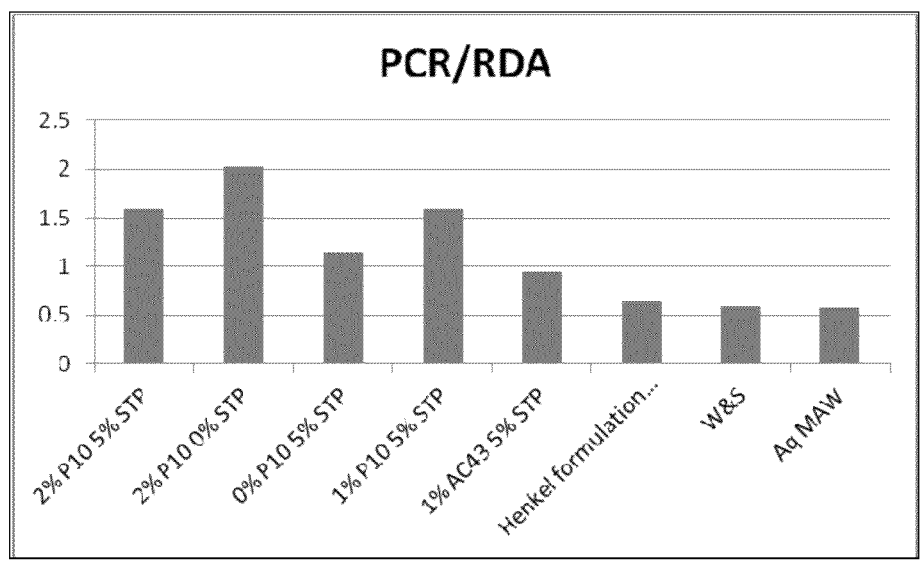
FIG. 3 is a graphic depiction of the Cleaning Efficiency Index of the formulations from the PCR Methodology and the RDA Methodology.

The Cleaning Efficiency Index data (see FIG. 3) demonstrate that compositions of the present invention containing an alumina polishing agent with a condensed phosphate provide highly effective cleaning at low RDA levels; certainly more effectively than a Henkel formulation containing an alumina polishing agent together with a silica abrasive and a condensed polyphosphate. Contrary to the teaching in the above-noted Henkel patent (U.S. Pat. No. 6,517,815) it is apparent that the inclusion of a silica abrasive reduces the cleaning efficiency of the compositions of the present invention comprising the combination of an alumina abrasive and a condensed phosphate; free of silica abrasive. Whilst the Henkel formulation provides good cleaning as measured by PCR the presence of the silica abrasive significantly increases the RDA of the formulation thereby reducing its cleaning efficiency.

Gloss Methodology

For each test paste, 8 bovine enamel specimens were prepared to grit 400/P 800 followed by 5 minutes ultrasonication in tap water, and were then surface profiled. ADA/ISO standard tape was used to cover the unbrushed reference area and only a test band of the enamel specimen was exposed. The enamel specimens were mounted in two brushing channels of the Ctrl-16 brushing simulator. Oral B P35 toothbrushes were used for the brushing. Specimens were double brushed sequentially for 5000 strokes at a brushing speed of 120 rpm and a temperature of 20° C. was maintained throughout the whole brushing procedure. The slurry diluents were prepared with 25 g toothpaste in 40 ml water. 150 g slurry was used in each channel and a brushing load of 150 g was applied. After brushing for the requisite number of strokes, the tape was removed and any residue cleared by gently wiping with a wet tissue before thoroughly rinsing with water.

Figure 4:
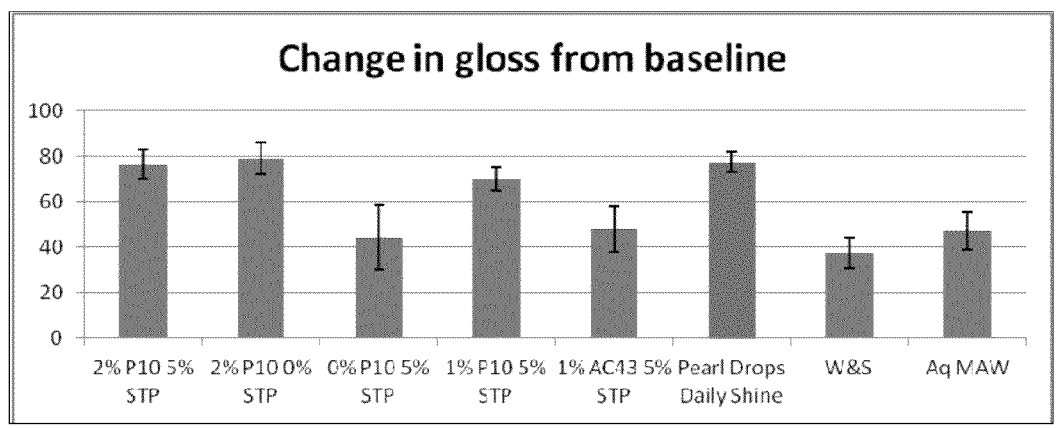
FIG. 4 is a graphic depiction of the Gloss for each test paste wherein the gloss measurements were taken before and after brushing with a Novo-Curve small area glossmeter.

Gloss measurements were taken before and after brushing with a Novo-Curve small area glossmeter, at intervals of 90 degrees rotation about the centre point of each specimen. See FIG. 4.

The values obtained in the above gloss and RDA experiments above were then used to obtain the following Gloss Efficiency Index (GEI) which is the Gloss/RDA value.

Figure 5:
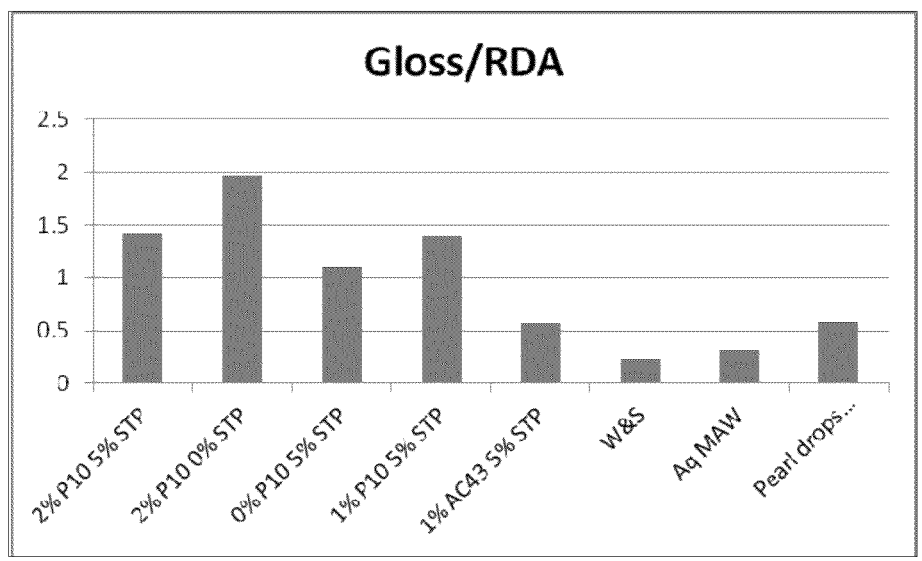
FIG. 5 is a graphic depiction of Gloss Efficiency Index (GEI) which is the Gloss/RDA value, demonstrating that compositions of the present invention containing an alumina polishing agent with a condensed phosphate provide highly effective polishing at low RDA levels.

As with the CEI data, the Gloss Efficiency Index data demonstrates that compositions of the present invention containing an alumina polishing agent with a condensed phosphate provide highly effective polishing at low RDA levels; certainly more effective than a commercial formulation containing an alumina polishing agent together with a silica abrasive and a condensed polyphosphate. Whilst this formulation provides good polishing, the presence of the silica abrasive significantly increases the RDA of the formulation thereby reducing its polishing efficiency. See FIG. 5.

From all of the above results it can be seen that the compositions of the present invention provide high gloss, very effective cleaning with low dentine abrasion.

The invention claimed is:

1. A method of whitening and polishing tooth enamel comprising administering a dentifrice composition comprising from 0.1% to 3.0% by weight of a calcined aluminium oxide polishing agent having a primary crystal size of <1 micron and comprising from 50% to 90% by weight of α-aluminium oxide and 10.0% to 50% by weight of γ-aluminium oxide, a sodium tripolyphosphate salt and an orally acceptable carrier or excipient; the composition being free of a silica abrasive.

2. The method according to claim 1 wherein the sodium tripolyphosphate salt of the dentifrice composition is present at a level from 1.0% to 20.0% by weight of the total composition.

3. The method according to claim 1 wherein the dentifrice composition additionally comprises one or more surfactants.

4. The method according to claim 1 wherein the dentifrice composition comprises a source of fluoride ions.

5. The method according to claim 4 wherein the fluoride ion source of the dentifrice composition is sodium fluoride.

6. The method according to claim 1 wherein the dentifrice composition comprises an anti-plaque agent.

7. The method according to claim 1 wherein the dentifrice composition comprises an oral anti-malodour agent.

8. A method according to claim 1 wherein the pH of the dentifrice composition is between 7.0-10.0.

* * * * *